US011085033B2

(12) United States Patent
Liu et al.

(10) Patent No.: US 11,085,033 B2
(45) Date of Patent: Aug. 10, 2021

(54) GLYCOSYLATED OXALATE DECARBOXYLASE AND PREPARATION AND APPLICATION THEREOF

(71) Applicant: WUHAN KANGFUDE BIOTECHNOLOGY CO., LTD., Wuhan (CN)

(72) Inventors: Haifeng Liu, Wuhan (CN); Baoping Song, Wuhan (CN); Xianqiao Chen, Wuhan (CN); Huoqing Chen, Wuhan (CN); Pei Tong, Wuhan (CN); Wei Wang, Wuhan (CN); Xiaofeng Wang, Wuhan (CN)

(73) Assignee: WUHAN KANGFUDE BIOTECHNOLOGY CO., LTD., Wuhan (CN)

( * ) Notice: Subject to any disclaimer, the term of this patent is extended or adjusted under 35 U.S.C. 154(b) by 0 days.

(21) Appl. No.: 15/743,641

(22) PCT Filed: Jul. 7, 2017

(86) PCT No.: PCT/CN2017/092149
§ 371 (c)(1),
(2) Date: Jan. 10, 2018

(87) PCT Pub. No.: WO2018/054132
PCT Pub. Date: Mar. 29, 2018

(65) Prior Publication Data
US 2020/0080070 A1 Mar. 12, 2020

(30) Foreign Application Priority Data
Sep. 23, 2016 (CN) .......................... 201610848095.1

(51) Int. Cl.
*C12N 9/88* (2006.01)
*A23K 20/189* (2016.01)
*A23L 29/00* (2016.01)
*A23L 33/10* (2016.01)
*C12N 1/14* (2006.01)
*A61K 38/00* (2006.01)

(52) U.S. Cl.
CPC .............. *C12N 9/88* (2013.01); *A23K 20/189* (2016.05); *A23L 29/06* (2016.08); *A23L 33/10* (2016.08); *C12N 1/14* (2013.01); *C12Y 401/01002* (2013.01); *A23V 2002/00* (2013.01); *A61K 38/00* (2013.01)

(58) Field of Classification Search
CPC .......... C12N 9/88; C12N 1/14; A23K 20/189; A23L 29/06; C12Y 401/01002
See application file for complete search history.

(56) References Cited

U.S. PATENT DOCUMENTS

| 5,547,870 A * | 8/1996 | Datta ....................... C12N 9/88 |
| | | 435/232 |
| 6,699,469 B2 | 3/2004 | Allison et al. |
| 8,142,775 B2 | 3/2012 | Shenoy et al. |
| 9,795,657 B2 * | 10/2017 | Cowley ................... A61P 13/02 |
| 2002/0061292 A1 | 5/2002 | De Simone |

FOREIGN PATENT DOCUMENTS

| CN | 00808182.4 | 8/2002 |
| CN | 101554237 A | 10/2009 |
| CN | 102697040 A | 10/2012 |
| CN | 103614359 A | 3/2014 |
| CN | 201610217032.6 | 6/2016 |
| WO | 2004018634 A2 | 3/2004 |
| WO | 2006/135925 A3 | 12/2006 |
| WO | WO-2016161455 A2 * | 10/2016 ........... A61K 9/0053 |

OTHER PUBLICATIONS

D. Goldfarb, et. al., "A randomized, controlled trial of lactic acid bacteria for idiopathic hyperoxaluria", Clin. J. Am. Soc. gephrol., 2:745-749, May 30, 2007.
R. Holmes et al., "The impact of dietary oxalate on kidney stone formation." Urol. Res. 32:311-316, Jun. 17, 2004.
Wei Cheng-yu;Lin Ri-hui;Long Han;Liang Yue;Xuan Jin-cai;Key Laboratory of New Techniques for Chemical and Biological Conversion Process,College of School Marine Science and Biotechnology,Guangxi University for Nationalities;;Study on chemical modification of oxalate decarboxylase by dextran[J] (2014).

* cited by examiner

*Primary Examiner* — Taeyoon Kim
*Assistant Examiner* — Tiffany M Gough
(74) *Attorney, Agent, or Firm* — Novick, Kim & Lee, PLLC; Allen Xue

(57) ABSTRACT

The present invention discloses a glycosylated oxalate decarboxylase. The oxalate decarboxylase is derived from edible basidiomycetes, the glycosylated oxalate decarboxylase has an enzyme activity at the pH value of 1.5-7.5, the activity at the pH value of 1.5-2.0 is 10% greater than the optimum activity, and a specific activity is more than 2 U/mg. The present invention also discloses preparation and application of the glycosylated oxalate decarboxylase. The glycosylated oxalate decarboxylase disclosed by the present invention can keep the activity under a low pH value, and can effectively prevent and treat kidney stones.

15 Claims, 4 Drawing Sheets

GLYCOSYLATED OXALATE DECARBOXYLASE AND PREPARATION AND APPLICATION THEREOF

CROSS REFERENCE TO RELATED APPLICATIONS

The entire content of the priority of the application of a Chinese patent (the Patent Application No.: 201610848095.1, titled as "Dry Powder and Fungus Powder Containing *Agrocybe aegerita* Oxalate Decarboxylase and Preparation Method and Application Thereof" and submitted to the State Intellectual Property Office of the P.R.C. on Sep. 23, 2016), is hereby incorporated by reference to this present application.

TECHNICAL FIELD

The invention relates to glycosylated oxalate decarboxylase and preparation and application thereof.

BACKGROUND

Kidney stones, 80% of which are calcium oxalate stones, cause pain to tens of millions of people around the world every year and billions of dollars of economic losses. In the United States, about 5 million persons enter the first aid rooms each year because of kidney stones, and it is also one of the seven major hospitalized diseases which cause an annual economic loss of about $5 billion. Each year, the kidney stone patient number is increased at a rate of 7-11%, the situation in China is similar to that in the United States. In addition, kidney stones are also the complication of many modern diseases (e.g., diabetes, obesity, etc.).

Oxalic acid is formed by the coupling of dicarboxylic acid connected via C—C bond. Under the condition of physiological pH value, sodium oxalate and potassium oxalate are soluble in water, but the solubility of calcium oxalate in water is less than 0.06 mM. The concentration of oxalic acid in the blood is 1-6 µM, far below the saturation of calcium oxalate. However, owing to the reabsorption of kidney on water, the concentration of oxalate in the kidney's concentrated crude urine is increased by more than a hundredfold. The concentration of calcium ions in urine is generally about 5 times that of oxalate, and thus, the concentration of calcium oxalate in the kidney is up to 0.1-0.6 mM, which is in the supersaturated state, and calcium oxalate in a highly supersaturated state can be precipitated into a solid, namely, growth calculus. Although the growth calculus is affected by the physiological state of the kidney, crude urine and other components in urine, the degree of supersaturation of calcium oxalate is the decisive factor for the formation and growth of the calculus.

The degree of supersaturation of calcium oxalate in urine is directly related to the source of oxalate in human blood. There are two paths for the sources of oxalate in the blood of the human body: the physiological metabolism of the human body and absorption from food. Except for the patients with primary hyperoxaluria, almost all people metabolize a certain amount of oxalate, but the amount of oxalate absorbed from food varies from person to person. The amount of oxalate absorbed by patients with urolithiasis is more than 50% higher than that of the normal persons (R. Holmes et al., Urol. Res. 32:311-316, 2004), so that calcium oxalate in the pelvis and urethra is significantly higher than its saturation. In the urinalysis of these patients, the amount of urinary oxalate is higher than that of normal people, known as hyperoxaluria. Most of patients with recurrent calcium oxalate stones are those with hyperoxaluria.

Almost all food contains oxalate, and a lot of food, especially some vegetables and cereals, contain high oxalate. Doctors often advise patients with urolithiasis to reduce the intake of oxalate by choosing the food with low oxalate, but there are a few varieties of food with low oxalate content, and the content of oxalic acid in such food is affected by the components of its growing soil, water content and climate, resulting in unreliable selection methods of edible food with low oxalate content and malnutrition. Therefore, people shall not choose it if there is another choice.

There is not a really effective medicine or good treatment method for kidney stones. Only some small stones (diameter or maximum size <0.6 cm) which are found early can be excreted through drinking a large amount of water and doing sports, however, and other treatment methods such as extracorporeal shock wave lithotripsy, percutaneous nephrolithotomy, or open surgical therapy to removal of the stones not only bring trauma to the body and kidney, but also pose a high recurrence rate and high operating expenses. Repeated use of these methods for recurrent patients will eventually lead to renal failure. Therefore, it is urgent to treat and prevent the recurrence of calculus through medicine.

The citrate medicament is the only drug for preventing calculus growth for 20 to 90 percent of patients with urolithiasis under the verification of the clinical trial, but it is mainly used for calcium urate stones. However, the patients need to take 6-10 grains of citrate daily for a long period of time. Citrate changes the composition of salts and acid-base balance in blood and urine. Because of large dosage and high side effects, many patients can't bear the side effects and have to stop treatment.

Degrading the oxalate in stomach with enzyme or microbes to reduce its absorption and further reduce the concentration of oxalate in urine has attracted people's attention. Except of enzyme or microbes can remove materials (oxalate) for growing calcium oxalate calculus, and prevent the formation, growth and recurrence of calcium oxalate stones, the enzyme or microbe method also has the advantages of safety, no trauma and the like.

The microbe method comprises the oral administration of microbes, such as a mixture product (CN00808182.4) of multiple *Bacillus* and *Bifidobacterium*, and an intestinally parasitic live bacterial formulation (U.S. Pat. No. 6,699,469) taking oxalate as energy substance. The former microbes are able to consume oxalic acid, however, because of the rich carbohydrates in the intestines, such microbes do not consume oxalic acid preferentially, and the clinical trials are proved to have no effect (D. Goldfarb, et. al., Clin. J. Am. Soc. Nephrol., 2:745-749, 2007); and the latter microbes only consume oxalic acid, but American Oxthera's Pharmaceutical Company completed two clinical trials and did not observe its ability to reduce urinary oxalic acid, and it is likely that oral live bacteria have not been able to colonize and survive in the intestinal tract.

After entering the stomach, the oxalate in the food is dissolved and released under the action of gastric acid with low pH value, and then, it is absorbed by the human body. Therefore, reduction in the absorption of diet oxalate should start from the stomach. The use of oral oxalate degrading enzymes to degrade oxalate in the stomach shall be more effective. The work in this area is mainly done by Altus and Oxthera. Altus Pharmaceutical made cross-linked enzyme crystals with an oxalate oxidase (PCT/US2006/023115) or an oxalate decarboxylase (U.S. patent application Ser. No.

11/833,082) (Altus-237, Altus), and these crystals are then made into oral preparations for the degradation of oxalate in the stomach. Altus Pharmaceutical's patent technology is inherited by Allena Pharmaceutical, which mainly focus on the oxalate decarboxylase cross-linked enzyme crystal. Clinical trials have shown that Allena Pharmaceutical found that the oral administration of high-dose enzyme preparations can only reduce urinary oxalate by 13% in patients with severe hyperoxaluria. Oxthera has prepared a preparation of another form, oxalate decarboxylase (OxDc) is mixed with an acid-insoluble polymer to prepare into microparticles by spray drying (Oxazyme, Oxthera). Clinical trials have shown that Oxazyme (Oxthera) does not reduce the effect of urinary oxalic acid.

Chinese patent application (No. 201610217032.6) announced a kind of oxalate decarboxylase produced by recombinant expression. There's an oxalate degrading enzyme activity at the pH value of 1.5-7.5, but because of the expression of the prokaryotic system, there is no glycosylated modification in the expressed oxalate degrading enzyme, the activity is not stable in the low pH value and high pH value, and the resistance to pepsin is weaker than that of the glycosylated oxalate decarboxylase (OxDc) in the present patent. Its activity is lower than the glycosylated oxalate decarboxylase of this patent.

SUMMARY

For the prior art, the oxalate decarboxylase preparation is inactive or unstable at a low pH value and the technical defect leads to that the urinary oxalate cannot be truly reduced. The invention provides a glycosylated oxalate decarboxylase, which can effectively reduce the content of urinary oxalate.

The technical scheme of the invention is as follows:

The present invention relates to a glycosylated oxalate decarboxylase. It is derived from an edible basidiomycetes and has enzyme activity when the pH value is 1.5-7.5; when the pH value is 1.5-2.0, the activity exceeds 10% of the optimal activity, and the specific activity is more than 2 U/mg. Preferably, when the pH value is 2.0-5.5; the activity exceeds 30% of the optimal activity, and the specific activity is more than 6 U/mg. Further preferably, the optimal pH environment for the enzyme activity of oxalate decarboxylase is pH2.5-3.0. Furthermore, when the oxalate decarboxylase is in the optimal pH range, the enzyme activity is 20-200 U/mg and the Kin value is 0.06 mM.

In one embodiment, the glycosylated oxalate decarboxylase involved in the invention is from edible *Agrocybe* fungus. Specifically, it can be selected from *Agrocybe aegerita*, *Agrocybe cylindracea*, *Agrocybe praecox* (Pers.) Fayod, *Agrocybe salicacola* or *Agrocybe pediades* (Fr.) Fayod.

In one embodiment, the oxalate decarboxylase is produced by liquid fermentation technology. In one specific embodiment, the induced production of the glycosylated oxalate decarboxylase via the liquid fermentation technology comprises the following steps: inoculating and culturing for 2 to 5 days, adjusting the pH value of fermentation broth to pH2.0-4.0 by adding acid to induce fungi to produce enzyme, and continuing to culture it for 7-10 days.

The invention also relates to a preparation method of the oxalate decarboxylase. According to the method, oxalate decarboxylase is produced with the use of biological fermentation by acid induction under the condition of 0.001-50 mM manganese ions. Strains for producing oxalate decarboxylase are from *Agrocybe* edible fungus.

In one specific embodiment, according to the preparation method of oxalate decarboxylase, when the enzyme is produced by induction, the pH value of the fermentation broth is adjusted to pH3.2~4.0, pH3.0~3.6, pH2.8~3.2, pH2.6~3.0 or pH2.0~2.8, preferably pH2.6~3.0 or pH2.8~3.2, and more preferably pH2.8~3.2; the acid used to adjust the pH value of the fermentation broth is organic acid or inorganic acid, preferably phosphoric acid, hydrochloric acid, citric acid and/or oxalic acid, more preferably phosphate and/or hydrochloric acid.

In one specific embodiment, the materials containing manganese ions added in the enzyme induction production of the preparation method of oxalate decarboxylase include $MnCl_2$, $MnSO_4$, $MnCO_3$, $Mn(NO_3)_2$ and/or $Mn(CH_3COO)_2$; the concentration of the added manganese ions is 0.001~0.1 mM, 0.1~1 mM, 1~2 mM, 2~4 mM, 4~6 mM, 6~10 mM or 10~50 mM, preferably 1~2 mM, 2~4 mM, 4~6 mM or 6~10 mM, and more preferably 2~4 mM or 4~6 mM.

In one specific embodiment, according to the preparation method of the oxalate decarboxylase, the feeding culture medium added in the induced enzyme production phase contained glutamic acid, arginine, aspartic acid or glutathione.

In one specific embodiment, according to the preparation method of the oxalate decarboxylase, the fermenter used in production is a mechanical stirring fermenter or an air lifting fermenter, preferably a mechanical stirring fermenter.

In one specific embodiment, according to the preparation method of enzyme powder containing the oxalate decarboxylase, the fermentation liquid obtained by fermentation is concentrated and purified, small molecular substances are removed, then the purified concentrate is dried into powder, i.e., the enzyme powder containing the oxalate decarboxylase.

In one specific embodiment, according to the preparation method of edible fungus powder containing oxalate decarboxylase, mycelia obtained by fermentation are filtered, washed, dried and crushed into fine powder, i.e., the edible fungus powder containing oxalate decarboxylase.

In one specific embodiment, the drying method in the preparation process of the enzyme powder containing the oxalate decarboxylase and the edible fungus powder containing the oxalate decarboxylase is a spray drying method, a vacuum freeze drying method or a vacuum drying method.

The invention also relates to an enzyme preparation containing the glycosylated oxalate decarboxylase. The enzyme preparation is for oral administration.

Specifically, the enzyme preparation is edible fungus powder, a feed additive, a feed, a food additive, food, a health care product, special medical food or a drug containing the glycosylated oxalate decarboxylase.

The invention further relates to the application of glycosylated oxalate decarboxylase and the oxalate decarboxylase in prevention and/or treatment of hyperoxaluria.

The invention further relates to the application of glycosylated oxalate decarboxylase and the oxalate decarboxylase in prevention and/or treatment of urinary calculi containing calcium oxalate.

The oxalate decarboxylase provided by the embodiments of the invention has stability, high activity and very high degradation efficiency on low-concentration oxalic acid in gastrointestinal environment, can be directly orally taken, is safe, and does not have any toxic or side effect.

The glycosylated oxalate decarboxylase and the related enzyme preparations provided in embodiments of the invention are stable and have high activity when the pH value is 1.5-7.5, have the Kin value of 0.06 mM at the optimal pH value (pH2.5-3.0), are significantly superior to the existing oxalate decarboxylase from *Bacillus subtilis*, and have the stability superior to oxalate decarboxylase obtained by recombinant expression of *Escherichia coli*.

The glycosylated oxalate decarboxylase and the related enzyme preparations thereof provided by the present invention are from *Agrocybe* edible fungi, which have a long history as human food, and are proved to be free of any toxic and side effects, so it is safe and can be taken for a long time.

DETAILED DESCRIPTION

Figure 1:
FIG. 1 depicts molecular weight identification of glycosylated oxalate decarboxylase and non-glycosylated oxalate decarboxylase (SDS-PAGE), wherein M is a protein molecular weight Marker; 1 is non-glycosylated oxalate degrading enzyme; and 2 is glycosylated oxalate degrading enzyme.

In the prior art, the application of oxalate decarboxylase does not achieve the useful clinical effect, which seems to show that it is not feasible to use oxalate decarboxylase to reduce the content of urinary oxalic acid. Upon a lot of experiments, the inventor is surprised to find that the main reason for the unsatisfactory pharmacodynamics of oxalate decarboxylase in the prior art is that the selected oxalate decarboxylase comes from the same kind of *Bacillus subtilis*, and has two major disadvantages (acid intolerance and high Kin value), thus resulting in incapability of survival and inefficient degradation of low-concentration oxalic acid in the stomach. The inventor supposed that the oxalate decarboxylase which could adapt to the acid gastrointestinal environment can achieve the effect to control the urinary oxalic acid content. The inventor screened thousands of types of edible materials and their different parts, involving plants, microbes, edible fungi, etc., and found that the oxalate decarboxylase of *Agrocybe* had high activity at a low pH value and could degrade oxalic acid in the acid environment of the stomach. However, because the content of oxalate decarboxylase is very low in the natural *Agrocybe* fungi, and it does not have the possibility of industrialization, so it is known that it creates a barrier to degrade oxalic acid in the acid environment of the stomach. The inventor of this application makes a lot of attempts to increase the yield of oxalate decarboxylase and realize its industrialization. The patent application (NO.: 201610217032.6) discloses a method for producing oxalate decarboxylase by using the expression of a prokaryotic expression system, in which the expression yield is greatly improved. However, the inventor finds a liquid culture and induction method enabling the agrocybe to naturally express oxalate decarboxylase through a lot of experiments, and surprisingly finds that the naturally expressed oxalate decarboxylase is of the same sequence as the oxalate decarboxylase expressed by the prokaryotic system, but it has significant advantages. By analyzing, the results show that the oxalate decarboxylase expressed by induction is glycosylated, so that it has significant advantages for improving the resistance to the low pH value in the stomach, the tolerance to pepsin and the enzyme activity. That is to say, the glycosylated oxalate decarboxylase has obvious advantages in treatment of hyperoxaluria over non-glycosylated oxalate decarboxylase.

The gene and the protein sequence of *Agrocybe aegirita* oxalate decarboxylase in the patent application are all the same as those of the *Agrocybe aegirita* described in the patent application (No. 201610217032.6). The application is introduced herein and will not be recorded repeatedly.

Since the pH in the stomach is very low, has non-uniform distribution, and is always changed, the pH value generally varies between pH1.5 and pH5.5, and the pH depends on the amount of food eaten, the type of food, the mixture of food and gastric acid, and the residence time in the stomach. In general, the pH value is low in an empty stomach, and the pH value is high when food with a great amount of meat is eaten. This requires that the enzyme products or drugs must be stable and have extremely high activity at the pH value of pH1.5 to pH5.5. In addition, the oxalic acid in the diet is generally present in the form of low soluble calcium oxalate and magnesium oxalate, resulting in low concentration of the soluble oxalic acid in the diet, generally between 0.05 and 0.5 mM. This requires high affinity of oxalate decarboxylase to oxalate, that is to say, the Kin value should be small. The oxalate decarboxylase of *Bacillus subtilis* is very unstable when the pH value is less than pH3.0, and is going to be denatured in a few seconds and loses the activity permanently. The pH value in the stomach is often lower than pH3.0. In addition, due to the constant secretion of gastric acid, the pH value in the whole stomach is not uniform, even if the average pH value in the stomach is above 3.0, there is still a pH value below pH3.0 locally. This is the main reason for the poor effect of the *Bacillus subtilis* OxDc enzyme. In addition, the enzyme has poor affinity to oxalate, and even under a condition of an ideal pH value, the Kin value is 4 mM. Moreover, prevention of hyperoxaliduria is a long-term process, so the patient needs long-term and even life-long administration. The *Bacillus subtilis* in the prior art has no historical habit of long-term administration by people. There is a potential risk of long-term administration of the oxalate decarboxylase from the *Bacillus subtilis*.

In order to screen a material containing an oxalate degrading enzyme that is stable and has a high activity in the gastrointestinal environment, that has a very high degradation effect on oxalic acid with a low concentration, and that is proved to be non-toxic and harmless for long-term administration by people, the inventor screens thousands of types of edible materials and their different parts, involving plants, microbes, edible fungi, etc., and finds that the enzyme activity and pH range of oxalate decarboxylase from basidiomycetes are suitable for the human gastrointestinal environment. The enzyme activity of the preferred *Agrocybe* edible fungi is stable and has a high activity at the pH value of pH1.5-7.5. Through a large number of experiments, the inventor finally finds a method for the cultivation of basidiomycetes in a liquid culture to produce enough oxalate decarboxylase, which can be used for experimental analysis and practical application. The oxalate decarboxylase produced by basidiomycetes has been glycosylated compared with the oxalate decarboxylase expressed by *Escherichia coli*. The stability of the glycosylated oxalate decarboxylase is significantly higher than that of the non-glycosylated oxalate decarboxylase at low pH values. The specific activity of the enzyme is increased significantly, and the resistance to pepsin and trypsin is better.

Embodiment 1

In this embodiment, *Agrocybe aegerita* is taken as an example to elaborate the fermentation process of glycosylated oxalate decarboxylase. In the experiments, the conclusions of *Agrocybe aegerita* are basically the same as those of *Agrocybe cylindracea*, *Agrocybe praecox* (pers.) fayod, *Agrocybe salicacola* and *Agrocybe pediades* (Fr.) fayod, and except part of the comparison results, this application does not set forth them.

*Agrocybe aegerita* is selected as the strain to cultivate and produce oxalate decarboxylase by shake flask. The culture medium formula is as follows: yeast extract 4 g/L, soy peptone 3 g/L, $KH_2PO_4$ 2 g/L, $MgSO_4 \cdot 7H_2O$ 0.2 g/L, $CaCl_2$ 1 g/L, glucose 20 g/L, corn starch 10 g/L and vitamin $B_1$ 10 mg/L. The pH value is 5.0-6.0. The shake flask loading volume is about 20-30%, and is sterilized at 121° C. for 30 minutes (vitamin $B_1$ was sterilized by filtration, and added into the culture medium before the inoculation). Pure *Agrocybe aegerita* mycelium cultivated on a PDA plate was inoculated to a sterilized fluid medium to produce oxalate decarboxylase as follows: culturing the mycelium (100 rpm-350 rpm) at 23-28° C. for 2-5 days, adding phosphoric acid into the broth to adjust its pH value to pH2.8-3.2 to induce OxDc production, and continuing to culture it for 7 days; collecting the fresh mycelium through filtration, washing it with citrate buffer solution (pH 3.0), placing the washed mycelium in a clean ceramic mortar, where liquid nitrogen is added to grind the mycelium into powder, and then adding citrate buffer solution (pH 3.0) into the powder and continuing to grind it into paste, which is then centrifuged (15,000 g) for 10 minutes; collecting the supernatant and the precipitate from the container, respectively, and placing them into new containers, wherein the mycelium precipitate becomes fungus powder containing oxalate decarboxylase after freeze-drying, while the supernatant becomes enzyme powder containing oxalate decarboxylase after freeze-drying; and taking the supernatant to purify and identify oxalate decarboxylase in Embodiment 2.

Embodiment 2: Purification and Identification Oxalate Decarboxylase

The supernatant containing oxalate decarboxylase obtained in Embodiment 1 is purified with Q sepharose chromatography to get purified oxalate decarboxylase. The operation process is as follows: adjusting the pH value of the supernatant containing oxalate decarboxylase to pH 6.0 with 0.5M NaOH, removing the precipitated impurities through high-speed centrifugation (15,000 g), and concentrating the supernatant with a 50 KDa ultrafiltration membrane; equilibrating the Q sepharose column by 5 column volumes (CV) by using 25 mM $NaH_2PO_4$ buffer solution (pH 6.0), loading the concentrated oxalate decarboxylase sample on the equilibrated Q sepharose column, and washing off the impure protein not bonding to the column with 2 CV equilibration buffer solution (25 mM $NaH_2PO_4$, pH 6.0), then gradiently eluting 5 CV with an elution buffer solution (elution buffer solution A: 25 mM $NaH_2PO_4$, pH 6.0; and elution buffer solution B: 25 mM $NaH_2PO_4$, 1M NaCl, pH 6.0), and collecting the components of the oxalate decarboxylase sample. The molecular weight of the purified glycosylated oxalate decarboxylase is 60-80 KDa by electrophoresis identification with denatured polyacrylamide gel (SDS-PAGE). The oxalate decarboxylase expressed in *Escherichia coli* is found to have a molecular weight of 45-50 KDa by electrophoresis identification with denatured polyacrylamide gel (SDS-PAGE). The molecular weight identification results of the two oxalate decarboxylases are as shown in FIG. 1.

Embodiment 3: Determination of Oxalate Decarboxylase Activity and its Enzymatic Property In this invention, high performance liquid chromatography (HPLC) is used to determine the activity of oxalate decarboxylase. The operation process is as follows: preheating 1.0 mL 5 mM (mmol/L) oxalate solution (25 mM citrate buffer solution contained, pH 3.0) at 37° C. for 10 min and adding 0.01-0.1 ml (added volume is adjusted according to enzyme concentration) solution containing oxalate decarboxylase or fungus powder suspension into the oxalate solution for reaction; adding 50 μL 2.5M (molar concentration) $H_2SO_4$ to inactivate the enzyme after reacting for 30 minutes; quickly centrifuging the reaction solution and collecting supernatant to determine the concentration of residual oxalate by using HPLC. One enzyme activity unit (U) is defined as the required enzyme amount to degrade 1 micromole oxalate per minute on this condition.

Figure 2:
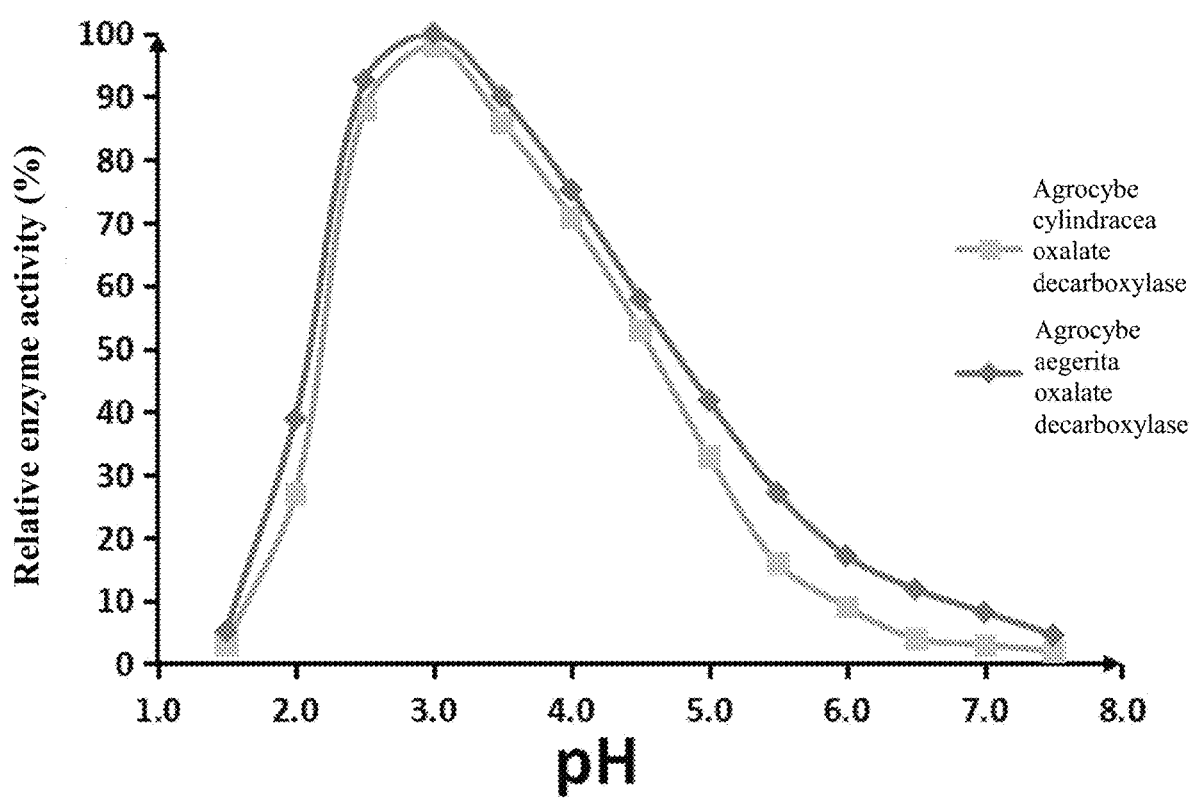
FIG. 2 depicts relative activity of glycosylated oxalate decarboxylase in different pH values.

The enzyme activity of the purified glycosylated oxalate decarboxylase obtained in Embodiment 2 was determined at pH 3.0, and the result is shown in Table 1. The oxalate decarboxylases of *Agrocybe aegerita* and *Agrocybe cylindracea* are taken as an example to determine the relative enzyme activity at different pH values from pH 1.5 to pH 7.5, and the results (FIG. 2) show that the OxDc are active at pH 1.5-7.5. What's more, they are highly active in the gastric environment (pH 1.5~5.5). The oxalate decarboxylase of *Agrocybe aegerita* is taken as an example to determine its Kin value with a double reciprocal method, and the result shows that the Kin value is very small, so it is fluctuant at different determination process. Different enzyme batches show the Kin value between 0.03 and 1.0 mM at different pH (pH 2.5-6.0), and the average Kin value at optimal pH range of pH 2.5-3.0 is 0.06 mM, as is shown in Table 2.

TABLE 1

Specific activity of different oxalate decarboxylases

| Strain | Specific Activity (U/mg) |
| --- | --- |
| Agrocybe Aegerita | 130 |
| Agrocybe Cylindracea | 100 |
| Agrocybe Praecox (Pers.) Fayod | 20 |
| Agrocybe Pediades Fayod | 200 |
| Agrocybe Pediades (Fr.) Fayod | 153 |

TABLE 2

Km value determination of oxalate decarboxylase at different pH values

| Range of pH Value | Km Value (mM) |
|---|---|
| 2.5-3.0 | 0.06 ± 0.03 |
| 3.0-3.5 | 0.12 ± 0.04 |
| 3.5-4.0 | 0.20 ± 0.03 |
| 4.0-4.5 | 0.25 ± 0.08 |
| 4.5-5.0 | 0.36 ± 0.13 |
| 5.0-6.0 | 0.7 ± 0.30 |

Figure 3:
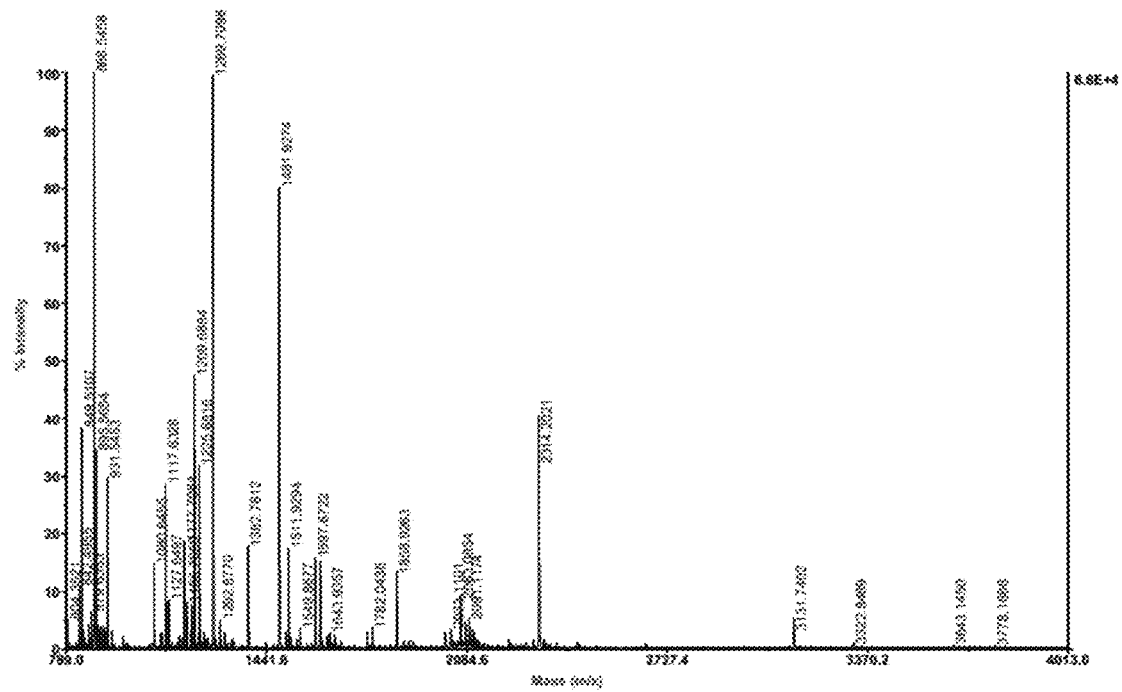
FIG. 3 depicts MALDT-TOF-MS peptide mass spectrometry of glycosylated oxalate decarboxylase.

Embodiment 4: Peptide Mapping Analysis on Glycosylated Oxalate Decarboxylase The purified glycosylated oxalate decarboxylase of *Agrocybe aegerita* in Embodiment 2 was digested with TPCK treated trypsin and analyzed by MALDI-TOF-MS. The result is shown in FIG. 3 (molecular weight list of mass spectrum).

TABLE 3

Molecular weight list of peptide mapping mass spectrum of glycosylated oxalate decarboxylase

| Serial Number | Molecular Weight (Da) | Oxalate decarboxylase Sequence Fragment |
|---|---|---|
| 1 | 804.3521 | |
| 2 | 842.4955 | |
| 3 | 879.6353 | VKPIVVGPA |
| 4 | 888.5458 | LQTGGWAR |
| 5 | 895.5654 | |
| 6 | 920.5276 | |
| 7 | 1080.6455 | TAEWAYVLK |
| 8 | 1117.6328 | WAFSLSHNR |
| 9 | 1127.6497 | |
| 10 | 1177.7084 | |
| 11 | 1185.7059 | VPPMQLSGGTAK |
| 12 | 1209.6884 | MTIFAAQSNAR |
| 13 | 1225.6816 | |
| 14 | 1269.7098 | NFQTDISAFAR |
| 15 | 1292.677 | |
| 16 | 1382.7612 | |
| 17 | 1481.9274 | AIAAAEVTIEPGAIR |
| 18 | 1503.8977 | |
| 19 | 1549.8677 | |
| 20 | 1597.8722 | AHLGFDDATMAHLAK |
| 21 | 1643.9357 | GSLGATIIGPTDVDTTK |
| 22 | 1782.0438 | |
| 23 | 1858.9263 | |
| 24 | 2063.0854 | |
| 25 | 2033.1101 | ANPDLLAPPTTDHGSVDNAK |
| 26 | 2091.1174 | EQNIGVMPIATEMASVNMR |
| 27 | 2103.1228 | |
| 28 | 2314.2021 | ELHWHPTQDEWSFFIEGR |
| 29 | 3131.7402 | |
| 30 | 3322.8489 | |
| 31 | 3643.145 | |
| 32 | 3778.1868 | |

Embodiment 5: Comparison of Glycosylated Oxalate Decarboxylase and Non-Glycosylated Oxalate Decarboxylase In this embodiment, oxalate decarboxylase of *Agrocybe aegerita* is taken as an example to compare the enzymatic property of glycosylated oxalate decarboxylase with that of non-glycosylated oxalate decarboxylase. Oxalate decarboxylase genes of *Agrocybe aegerita* were recombined expressed according to the operation method of invention patent application (201610217032.6), and purified to obtain non-glycosylated oxalate decarboxylase. The enzymatic property and stability of the oxalate decarboxylase were compared with those of the glycosylated oxalate decarboxylase of *Agrocybe aegerita* obtained in Embodiment 2 by purification.

Figure 4:
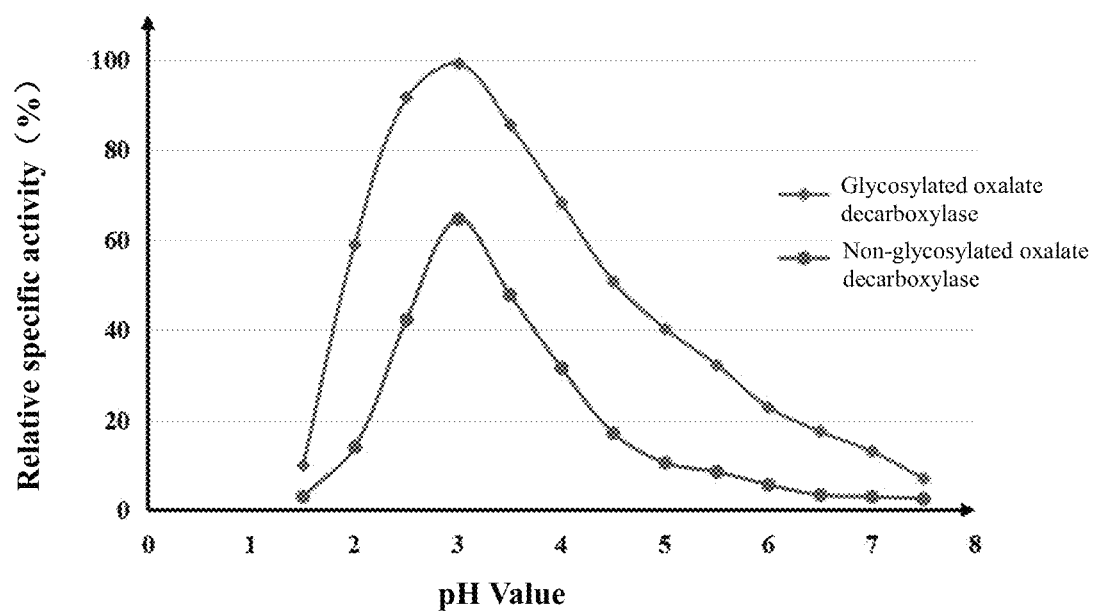
FIG. 4 depicts comparison of specific activities of glycosylated oxalate decarboxylase and non-glycosylated oxalate decarboxylase.

(1) Specific Activity Comparison:

The specific activity comparison is as follows: determining the protein concentrations of non-glycosylated oxalate decarboxylase expressed in *Escherichia coil* and the glycosylated oxalate decarboxylase expressed in *Agrocybe aegerita* with a Coomassie brilliant blue method, adjusting them to the same protein concentration (0.5 mg/ml), and determining the specific activities of the two oxalate decarboxylases in buffer solutions of different pH values with the method described in Embodiment 3; defining the specific activity of glycosylated oxalate decarboxylase at the optimum pH value as 100%, and comparing its specific activity at different pH values as well as the specific activity of non-glycosylated oxalate decarboxylase at different pH values with it. According to the result shown in FIG. 4, the activity of the glycosylated oxalate decarboxylase is significantly higher than that of non-glycosylated oxalate decarboxylase (>30%).

Figure 5:
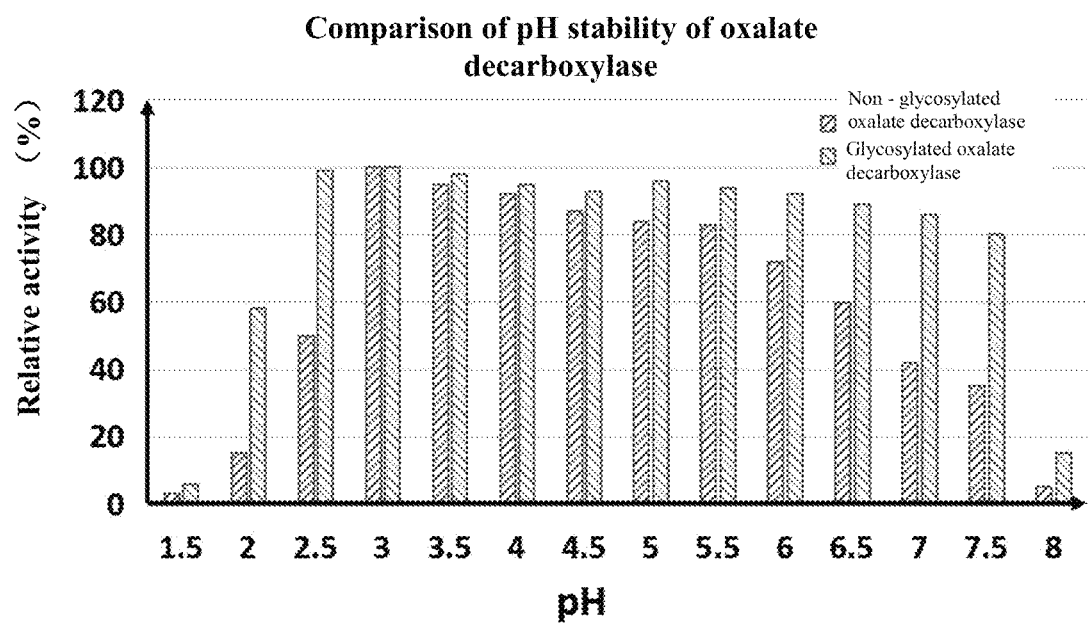
FIG. 5 depicts comparison of pH stability of glycosylated oxalate decarboxylase and non-glycosylated oxalate decarboxylase.

(2) Stability Comparison:

The stability comparison is as follows: adjusting the non-glycosylated oxalate decarboxylase sample expressed in *Escherichia* coli and the glycosylated oxalate decarboxylase sample expressed in *Agrocybe aegerita* to the same enzyme activity concentration, adding them to buffer solutions with pH 1.5, pH 2.0, pH 2.5, pH 3.0, pH 3.5, pH 4.0, pH 4.5, pH 5.0, pH 5.5, pH 6.0, pH 6.5, pH 7.0, pH 7.5 and pH 8.0, respectively, incubating them for 30 minutes at 37° C., taking a sample of 25 µL from each of them, adding each sample into 10 mL 5 mM oxalate reaction solution (25 mM citrate buffer solution contained, pH value of 3.0) preheated at 37° C., then reacting them for 30 minutes at 37° C., and adding 50 µL 2.5M $H_2SO_4$ into the reaction solution to stop reaction; centrifuging the reaction solution immediately and collecting supernatant for activity determination by HPLC; determining the activities of oxalate decarboxylase in the samples by adopting the HPLC method, defining the activity of an original sample as 100%, and calculating the activity of residual oxalate decarboxylase in the sample after being processed by different pH buffer solutions, wherein the results are as shown in FIG. 5. The results showed that the stability of the glycosylated oxalate decarboxylase to a pH value is obviously superior to that of the non-glycosylated oxalate decarboxylase, especially the stability of oxalate decarboxylase at strong acid conditions (pH value<2.5) or neutral or weak base conditions (pH value>5.5).

(3) Comparison of Resistance to Proteinase

The comparison is as follows: preparing samples of glycosylated oxalate decarboxylase and non-glycosylated oxalate decarboxylase to into solutions of 10 U/mL, respectively, taking 1 mL OxDc sample respectively and mixing it with 20 mL 50 mM hydrochloric acid buffer solution (pH 2.5) containing 10 mg/mL pepsin, then stirring and incubating it at 37° C. for 5 minutes, 10 minutes, 20 minutes, 40 minutes and 60 minutes, respectively, and sampling it at the time point above to analyze the activity of residual oxalate decarboxylase. The results are as shown in Table 4.

TABLE 4

Comparison of resistance to pepsin of glycosylated and non-glycosylated oxalate decarboxylases

|  | Control | 5 minutes | 10 minutes | 20 minutes | 40 minutes | 60 minutes |
|---|---|---|---|---|---|---|
| Glycosylated oxalate Degrading Enzyme | 100% | 95% | 88% | 75% | 65% | 58% |
| Non-Glycosylated oxalate Degrading Enzyme | 100% | 85% | 72% | 63% | 50% | 34% |

Embodiment 6: Removal of Oxalic Acid from Food with Oxalate Decarboxylase

Almost of all kinds of food, beverages, Chinese herbal preparations and feeds made with plants as raw materials contain oxalate, and its content in green vegetables, chocolate, cocoa, peanut and its products, soybean and bean products, tea and tea drinks, coffee and various wheat and grains is very high. Oxalate decarboxylase can be prepared into food additives or drugs to eat together with food, and degrades beverages and food's oxalate in the stomach to prevent excess oxalate from being absorbed by the gastrointestinal tract. Application of enzyme powder and edible bacterial powder containing oxalate decarboxylase that is prepared in the embodiments of this invention will be explained below.

(1) Removal of Oxalate from Tea 1-40 mg oxalate is contained in 1 L tea water, and its content depends on tea type, producing area, concentration and preparation method. The removing process is as follows: taking 20 g green tea, adding it in hot water of 90-95° C. for 5 minutes, filtering out tea leaves, then adjusting its pH value to pH 3.0-4.0 when the water temperature is lowered to less than 50° C., adding 20 U oxalate decarboxylase of *Agrocybe aegerita* into the tea water, and stirring it for reacting 2 hours, wherein the results of oxalate concentration in green tea determined at different time points are as shown in Table 5. The results show that nearly all the oxalate in tea water is ici removed after 2 hours by the oxalate decarboxylase of *Agrocybe aegerita* prepared in this invention. This embodiment is fit for making oxalic acid-free bottled tea water, iced tea or tea granules, and it is also suitable for removing oxalate from many Chinese herbal preparations.

(2) Removal of Oxalate from Bean Products

Oxalate content is very high in dry soybean, so various kinds of bean products contain abundant oxalate. As daily foods of Asian people, soybean products are also important sources of protein. Therefore, removing oxalate from bean products is of great significance to those people suffering from enteric hyperoxaluria. The removing process is as follows: adjusting the pH value of soybean milk to pH 3.0-4.0, then adding oxalate decarboxylase of *Agrocybe praecox* (Pers.) fayod prepared in the embodiments of this invention into the soybean milk, and stirring the soybean milk until oxalate decreased to certain content, wherein the oxalate concentration in soybean milk determined at different time points is as shown in Table 5. The time needed to degrade oxalate depends on its content in soybean milk and the enzyme amount added. If 0.1 g oxalate is contained in 1 L soybean milk, and 1,200-unit oxalate decarboxylase is added in each 10 L soybean milk, 2 hours would be needed to stir it for oxalate removal.

TABLE 5

|  | 0 minutes | 10 minutes | 30 minutes | 60 minutes | 120 minutes |
|---|---|---|---|---|---|
| Green Tea | 100% | 65% | 27% | 5% | 3% |
| Black Tea | 100% | 59% | 32% | 6% | 2% |
| Soybean Milk | 100% | 89% | 67% | 34% | 8% |

Figure 6:
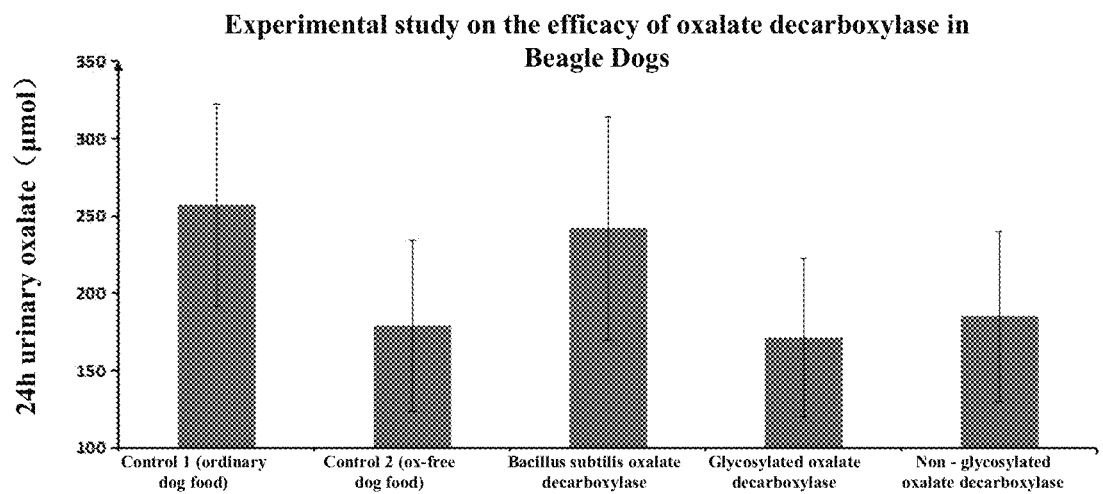
FIG. 6 depicts experimental result diagram of the ability of oxalate decarboxylase of different sources to degrade oxalic acid in food.

Embodiment 7: Animal Experiment to Reduce Urinary Oxalic Acid Content with Oxalate Decarboxylase The test process is as follows: feeding 6 male beagles, weighing 7-8 kg, purchased from Hubei Anlu Ruikesen Experimental Animal Co., Ltd., in standard independent dog cages; after their acclimatization for 3-5 days, feeding them with prepared oxalate-free food (Ox-free dog food), collecting 24 h urine, and determining total oxalic acid content; determining the content of oxalic acid in urine for 5 consecutive days when it was kept a stable value, and recording the average as low oxalic acid excretion; then feeding them with commercially available ordinary dog food (ordinary dog food), collecting 24 h urine, determining oxalic acid excretion in urine for 5 consecutive days, and recording the average as normal oxalic acid excretion; then successively feeding them with 1,000 U oxalate decarboxylase (OxDc) samples of different sources (*Bacillus subtilis* (patent number: 201080029636.9)), glycosylated oxalate decarboxylase (this patent) and non-glycosylated oxalate decarboxylase (patent number: 201610217032.6)) together with ordinary food, collecting 24 h urine for 5 consecutive days, determining oxalic acid excretion in urine, recording the mean value of total oxalic acid amount of the 5 days as oxalic acid excretion in urine, and evaluating the oxalic acid degrading ability of oxalate decarboxylase from different strain sources, wherein the result is as shown in FIG. 6. The 24-hour oxalic acid excretion in urine decreases to 242 μmol from 256 μmol of control group in the 1,000 U *Bacillus subtilis* oxalate decarboxylase group, to 185 μmol in non-glycosylated oxalate decarboxylase group, and to 171 μmol in glycosylated oxalate decarboxylase group, which is similar to oxalic acid excretion of feeding oxalic acid-free dog food (179 μmol). The results show that oxalate decarboxylase can degrade the oxalic acid of diet to varying degree, reduce the oxalate absorption, and hence reduce oxalate excretion. Compared with oxalate decarboxylase from *Bacillus subtilis*, the enzyme powder in glycosylated oxalate decarboxylase has better efficacy in reducing oxalic acid, almost the same as the effect on diet without oxalic acid. It can be used to treat enteric hyperoxaluria.

Figure 7:
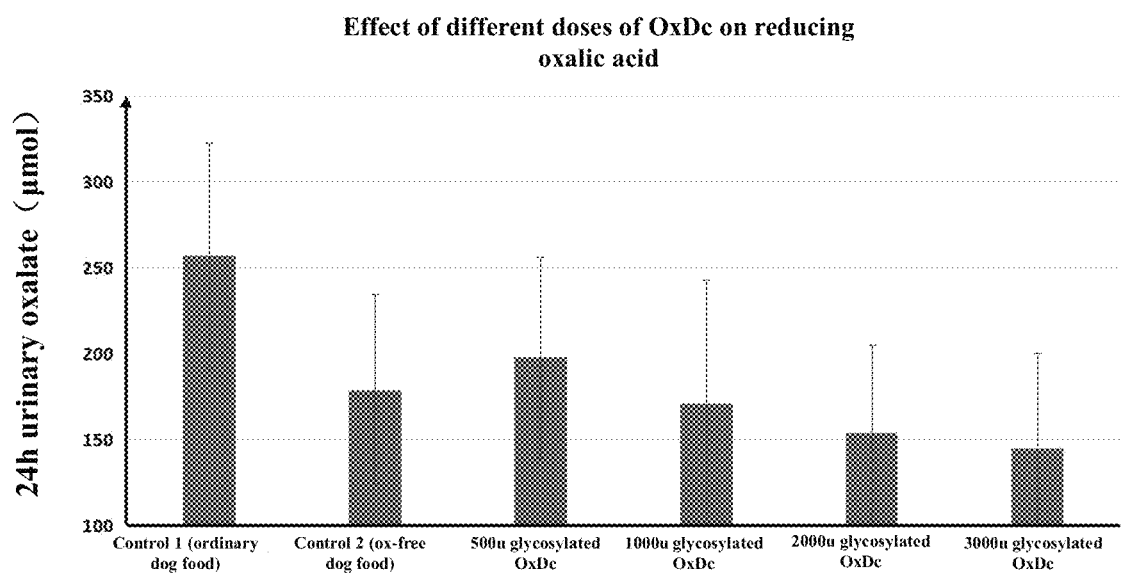
FIG. 7 depicts experimental result diagram of the ability of different dosages of *Agrocybe aegirita* oxalate decarboxylase to degrade oxalic acid in food.

The test process is as follows: feeding six Beagles, male, weighing 7-8 kg, purchased from Hubei Anlu Ruikesen Experimental Animal Co., Ltd. in a standard independent dog cage, acclimatizing them for 3-5 days, then feeding them the prepared oxalate-free food (Ox-free food), collecting 24 h urine, and determining the total amount of urine oxalic acid; after the oxalic acid in urine is steady, determining it for 5 successive days, recording the average value of oxalic acid excretion as low oxalic acid excretion; while feeding with the marketed ordinary food, feeding them with 500 U, 1000 U, 2000 U and 3000 U enzyme powder containing the glycosylated oxalate decarboxylase in turn, wherein the test period of each sample is 5 days; collecting 24 h urine, and determining urine oxalic acid excretion to evaluate the ability of different doses of glycosylated oxalate decarboxylase to degrade oxalic acid in food. The results are shown in FIG. 7. The results show that along with the increase of the dosage of the glycosylated oxalate decarboxylase, the ability to degrade oxalic acid is gradually strengthened. When the dosage is over 2,000 U, the excretion of urinary oxalic acid decreases from 256 μmol of the control group to 154 μmol, lower than that of the oxalic acid-free food group (179 μmol), indicating that the metabolism of part oxalic acid can also be degraded by oxalic acid degrading enzymes. Therefore, the glycosylated oxalic acid degrading enzyme can be applied to the treatment of primary hyperoxaluria.

Embodiment 8: Effect of Different Induction Conditions on the Production of Oxalate Decarboxylase This embodiment describes the effect of different induction conditions on enzyme production of oxalate decarboxylase of *Agrocybe* fungi. The specific operation is as follows:

*Agrocybe aegirita* is selected as the strain to cultivate and produce oxalate decarboxylase by a shake flask. The culture medium formula is as follows: yeast extract 4 g/L, soybean peptone 3 g/L, $KH_2PO_4$ 2 g/L, $MgSO_4.7H_2O$ 0.2 g/L, $CaCl_2$ 1 g/L, glucose 20 g/L, corn starch 10 g/L, vitamin $B_1$ 10 mg/L. The pH value is pH 5.0-6.0. The shake flask loading volume is 20-30%, and the culture medium is sterilized at 121° C. for 30 minutes (Vitamin $B_1$ is sterilized by filtration, and added to the culture medium before inoculation). The mycelia of *Agrocybe aegirita* cultured on PDA plate were inoculated into 3 groups (6 shake flasks) of the sterilized liquid culture medium while amount of inoculation is kept consistent as follows: culturing the mycelia (100 rpm-350 rpm) at 23-28° C. for 2-5 days; for Group 1 (shake flasks No. 1 and No. 2), adding hydrochloric acid to adjust the pH value to pH 2.8-3.2, and culturing it for 7-10 days to produce enzyme by induction; for Group 2 (shake flasks No. 3 and No. 4), adding 1.0 mM $MnCl_2$ and hydrochloric acid to regulate the pH value to pH 2.8-3.2, and then culturing it for 7-10 days to produce enzyme by induction; for Group 3 (shake flasks No. 5 and No. 6), adding sterilized distilled water of equal volume, and culturing it for 7-10 days to produce enzyme by induction; determining the activity of oxalate decarboxylase by suspension (refer to Embodiment 3 for the determination of enzyme activity) after the fermentation culture is homogenized in a high speed homogenizer. As a result (table 6), the enzyme activity of the acid-induced and manganese-added group (group 2) is significantly higher than that of the acid-induced group (group 1) and the control group (group 3). The enzyme activity of the acid induction group (group 1) is also significantly higher than that of the control group (group 3).

TABLE 6

| Flask No. | Acid-induced group (Group 1) | | Acid-induced and manganese-added group (Group 2) | | Control group (Group 3) | |
| --- | --- | --- | --- | --- | --- | --- |
| | 1 | 2 | 3 | 4 | 5 | 6 |
| Enzyme activity (U/L) | 2007 | 1761 | 5247 | 5560 | 3 | 5 |

Embodiment 9: Effect of Mycelium Pellet on Enzyme Activity

This embodiment provides the effect of mycelium pellet control on the activity of oxalate decarboxylase during the fermentation process by comparing the fermentation of two 7 L fermenters. The specific steps are as follows:

1) *Agrocybe aegirita* is taken as the strain, and a seed solution is cultivated by adopting a shake flask and divided into two portions. The seed culture medium is as follows: yeast extract, 4 g/L soy peptone, 6 g/L, $KH_2PO_4$, 1 g/L, $MgSO_4.7H_2O$, 0.5 g/L, $CaCl_2$, 0.1 g/L, glucose, 20 g/L, corn starch, 10 g/L, vitamin $B_1$ 10 mg/L. The pH value is pH5.0 to 6.0. The shake flask loading volume is 20~30%. The strain is cultured at 23-28° C. for 3 days under 100-350 rpm. Mycelium pellets are crushed with a hand-held emulsifier before one portion of the seed solution is inoculated into the fermentation culture medium, and the other portion of the seed solution is directly transferred into the fermentation culture medium as control. The inoculation amount is 10-30%;

2) The fermentation medium comprises the following components: yeast extract 4 g/L, soy peptone 3 g/L, $KH_2PO_4$ 2 g/L, $Na_2HPO_4$ 1 g/L, $MgSO_4.7H_2O$ 0.2 g/L, $CaCl_2$ 1 g/L, glucose 10 g/L, sucrose 20 g/L, corn starch 5 g/L, vitamin $B_1$ 10 mg/L. The shake flask loading volume is 70%. The pH value of the medium is adjusted to pH 4.5-6.5. The glucose and other components in the medium are sterilized separately. The glucose is sterilized at 115° C. for 15 min and the other components are sterilized together with the glass fermenter at 121° C. for 25 min. After the seed solution is inoculated into 7 L fermenter, the initial culture conditions of the two fermenters are as follows: temperature, 26° C.; stirring speed, 150 rpm; aeration volume, 3 L/min. During the fermentation process, the DO is controlled to greater than 40% by adjusting the stirring speed and the aeration volume. The pH value is adjusted to pH 2.8-3.2 by adding phosphoric acid for induction after fermentation for 3 days (72 h). Meanwhile, $MnCl_2$ is added to final concentration of 5 mM to induce the OxDc production for about 7 days. The size of mycelium pellets at different time points is detected by sampling after inoculation, the enzyme activity change of the fermentation broth is detected at the same time, and the details are as follows (Table 7):

TABLE 7

| Fermentation time | 7 L-1 (non-emulsified) Mycelium morphology | 7 L-2 (emulsified) Mycelium morphology |
|---|---|---|
| 40 h | The hyphae are elongated. There are many mycelium pellets, and its' diameters are between 200 μm and 500 μm. | The hyphae are dispersed. There are less mycelium pellets, and its' diameters are between 50-300 μm. |
| 64 h | The mycelium gradually becomes short, and the mycelium pellets gradually become thick; the mycelium pellets with the diameter of 400 μm-800 μm are increased; | The scattered hyphae are decreasing, the tiny mycelium pellets are also gradually bigger, and the diameters of the mycelium pellet maintain between 100 μm-300 μm; |
| 72 h (induced) | The hyphae around the mycelium pellets are getting shorter, and the size of the mycelium pellets basically maintain between 600 μm-1,000 μm; | The hyphae around the mycelium pellets are getting shorter, and the size of the mycelium pellets is almost not changed; |
| 118 h | The size of the mycelium pellets is basically kept between 700 μm and 1,200 μm; the hyphae around the mycelium pellets showed a decreasing trend; | The size of the mycelium pellet is basically maintained between 200 μm-500 μm, and the hyphae around the mycelium pellets are less than that of the hyphae when being induced. |
| 200 h | The change of mycelium pellets is not obvious, and there's less and less hyphae around the mycelium pellets; | The change of mycelium pellets is not obvious, there's less and less hyphae around the mycelium pellet, but there are more hyphae around the mycelium pellet; |
| 240 h | Total activity 15,000 U/L | Total activity 21,500 U/L |

After nearly 10 days of fermentation, the enzyme activity in the fermenter (7L-1) with mycelium pellets uncontrolled reaches 15,000 U/L, but the enzyme activity in the fermenter (7L-2) with mycelium pellets emulsified and controlled is 21,500 U/L. Compared with the uncontrolled mycelium pellets, the final oxalate decarboxylase activity of the controlled the mycelium pellet is improved by 43%.

Embodiment 10

This embodiment provides a preparation method of enzyme powder and edible fungus powder containing oxalate decarboxylase, comprising the specific steps as follows:

1) *Agrocybe aegirita* is taken as the strain and the seed solution is cultured in a shake flask. The components of seed medium are as follows: yeast extract 4 g/L, soy peptone 3 g/L, $KH_2PO_4$ 2 g/L, $MgSO_4 \cdot 7H_2O$ 0.2 g/L, $CaCl_2$ 1 g/L, glucose 20 g/L, corn starch 10 g/L, vitamin $B_1$ 10 mg/L, The pH value is pH 5-6. The loading volume in the shake flask is 20-30%. The strain is cultured at 23-28° C. for 2-5 days under 100-350 rpm. The mycelium pellets are crushed by a mechanical crushing method, and then inoculated with 10-30% of inoculation to next-stage seed culture medium;

2) The seed solution mycelium pellets mechanically crushed are inoculated with 10%-30% of inoculation to a 7 L mechanical-stirring fermenter. The liquid fermentation medium consists of the following ingredients: yeast extract 4 g/L, soybean peptone 3 g/L, $KH_2PO_4$ 2 g/L, $Na_2HPO_4$ 1 g/L, $MgSO_4 \cdot 7H_2O$ 0.2 g/L, $CaCl_2$ 1 g/L, glucose 10 g/L, cane sugar 20 g/L, corn starch 5 g/L, vitamin $B_1$ 10 mg/L. The loading volume is 65-70%. The pH value of the culture medium is adjusted to pH4.5-6.5. The mycelium pellets are cultured at 25-28° C. for 3-5 days after inoculation under the stirring speed of 150-350 rpm. The DO is maintained at over 30% by adjusting the stirring speed. This stage is the growth stage of mycelium, and the size of the mycelium pellets is controlled to be less than 1 mm 3) Induced enzyme production stage: when the wet cell mass content of the mycelium reached 5-30% of total volume, the pH value of the fermentation broth is adjusted slowly to pH 2.6-3.0 at the rate of 1 pH unit per hour at the same time, $MnCl_2$ is added to the final concentration (5 mM) of manganese ions, and the induction production is carried out for 3-15 days. The size of the mycelium pellets is controlled to be not more than 0.5 mm in the induction process. Feeding medium (soybean peptone: 70-90 g/L, glucose 80-120 g/L, glutamic acid 5 mM) is added from the 3rd day of induction. After the enzyme production is finished, the fermentation broth and mycelium are collected.

4) The solid-liquid separation is carried out via the method of filtering the fermentation broth and mycelium through the frame filter, and then the supernatant of the fermentation broth is concentrated through ultrafiltration. The small molecules in the fermentation broth are removed and the concentrated solution of oxalate decarboxylase is finally obtained. The concentrated solution is dried by spray drying. An enzyme protective material is added while spraying and oxalate decarboxylase powder is collected. *Agrocybe aegirita* mycelium is obtained through frame filtering, and dried by vacuum freeze drying. The edible fungus powder containing oxalate decarboxylase is finally obtained by superfine grinding the dry mycelium.

Embodiment 11

This embodiment provides a preparation method of enzyme powder and edible fungus powder containing oxalate decarboxylase, comprising the specific steps as follows:

1) *Agrocybe aegirita* is taken as the strain and a seed solution is cultured in a shake flask. The components of seed medium are as follows: yeast extract 4 g/L, soy peptone 3 g/L, $KH_2PO_4$ 2 g/L, $MgSO_4 \cdot 7H_2O$ 0.2 g/L, $CaCl_2$ 1 g/L, glucose 20 g/L, corn starch 10 g/L, vitamin $B_1$ 10 mg/L, pH 5-6. The shake flask loading volume is 20-30%. The strain is cultured at 23-28° C., 100-350 rpm for 2-5 days. The mycelium pellets of seed culture are crushed by a mechanical crushing method, and then inoculated with 10-30% of inoculation to next-stage seed culture medium;

2) The seed solution mycelium pellets mechanically crushed are inoculated with 10%-30% inoculation to a 7 L air-lifting fermenter for fermentation culture. The liquid fermentation medium consists of the following ingredients: yeast extract 4 g/L, soybean peptone 3 g/L, $KH_2PO_4$ 2 g/L, $Na_2HPO_4$ 1 g/L, $MgSO_4.7H_2O$ 0.2 g/L, $CaCl_2$ 1 g/L, glucose 10 g/L, sucrose 20 g/L, corn starch 10 g/L, vitamin $B_1$ 10 mg/L. The loading volume is 65-70% and the pH value of the culture medium is adjusted to pH 4.5-6.5. The mycelium pellets are cultured at 23-28° C., 100-350 rpm for 3-5 days after inoculation. The DO is maintained over 30% by adjusting the airflow speed. This stage is the growth stage of mycelium, and the size of the mycelium pellets is controlled to be less than 1 mm 3) Induced enzyme production stage: when the wet cell mass content of the mycelium grows to 5-30% of total volume, the pH value of the fermentation broth is slowly adjusted to pH 2.6-3.0 at the rate of 1 pH unit per hour. At the same time, $MnCl_2$ is added to the final concentration of manganese ions of 0.5 mM, and induced production is carried out for 3-15 days. During induction, the size of the mycelium pellets is not more than 1 mm, and the feeding medium (soybean peptone 70-90 g/L, glucose 80-120 g/L, citric acid 1 g/L) is added from the 3rd day of induction. After the enzyme production is finished, the fermentation broth and mycelium are collected.

4) The solid-liquid separation is carried out by the method of filtering the fermentation broth and the mycelium through the plate frame filtration, and then the supernatant of the fermentation broth is concentrated by ultrafiltration and concentration. The small molecule substances in the fermentation broth are removed to obtain a concentrated solution. The concentrated solution is dried by spray drying. A protein protectant is added while spraying, and the oxalate decarboxylase powder is collected. *Agrocybe aegirita* mycelium is obtained through frame filtering, and dried by vacuum freeze drying to obtain dry mycelium, and the edible fungus powder containing oxalate decarboxylase is finally obtained by superfine grinding.

Embodiment 12

This embodiment provides a preparation method of enzyme powder and edible fungus powder containing oxalate decarboxylase, comprising the specific steps as follows:

1) *Agrocybe cylindracea* is taken as the strain and a seed solution is cultured in a shake flask. The components of seed medium are as follows: yeast extract 2 g/L, soybean peptone 1 g/L, $KH_2PO_4$ 3 g/L, $MgSO_4.7H_2O$ 1 g/L, $CaCl_2$ 0.1 g/L, glucose 30 g/L, corn starch 10 g/L, vitamin $B_1$ 5 mg/L. The pH value is pH 5.0-6.0. The shake flask loading volume is 20-30%. The strain is cultured at 23-28° C., 100-350 rpm for 2-5 days. The mycelium pellets of seed solution are crushed by a mechanical crushing method, and then inoculated with 10-30% of inoculation to next-stage seed culture medium;

2) The seed solution mycelium pellets mechanically crushed are inoculated with 10%-30% inoculation to a 7 L mechanical-stirring fermenter for fermentation culture. The liquid fermentation medium consists of the following ingredients: yeast extract 8 g/L, soybean peptone 3 g/L, $KH_2PO_4$ 1 g/L, $Na_2HPO_4$ 1 g/L, $MgSO_4.7H_2O$ 0.8 g/L, $CaCl_2$ 1 g/L, glucose 10 g/L, cane sugar 30 g/L, corn starch 15 g/L, vitamin $B_1$ 5 mg/L. The loading volume is 60-70% and the pH value of the culture medium is adjusted to pH 4.5-6.5. The mycelium pellets are cultured at 23-28° C., 100-350 rpm for 3-5 days after inoculation. The DO is maintained over 30% by adjusting the stirring speed. This stage is the growth stage of mycelium, and the size of the mycelium pellets is controlled to be less than 1 mm.

3) Induced enzyme production stage: when the wet cell mass content of the mycelium reaches 5-30%, the pH value of the fermentation broth is adjusted slowly to pH 2.0-2.8 at the rate of 0.5 pH unit per hour; at the same time, $MnSO_4$ is added to the final concentration of manganese ions of 5 mM, and the induction production is carried out for 3-15 days. The size of the mycelium pellets is controlled to be not more than 0.5 mm in the induction process. A feeding medium (soybean peptone: 70-90 g/L, glucose 80-120 g/L, formic acid 2 g/L) is added from the 4th day of induction. After the enzyme production is finished, the fermentation broth and mycelium are collected respectively.

4) The solid-liquid separation is carried out by the method of filtering the fermentation broth and the mycelium through the plate frame filtration, then the supernatant of the fermentation broth is concentrated by ultrafiltration and concentration, the small molecule substances in the fermentation broth are removed, and the final concentrated solution is dried by spray drying while protein protectant is added, to obtain oxalate decarboxylase powder. *Agrocybe cylindracea* mycelium is obtained through frame filtering, and dried by spray drying after homogenization, wherein the inlet temperature of the spray dryer is 170-190° C., the outlet temperature is 80-95° C., and the other parameters are adjusted according to the size of the spray dryer. Edible fungus powder containing oxalic acid degrading enzyme is finally obtained.

Embodiment 13

This embodiment provides a preparation method of enzyme powder and edible fungus powder containing oxalate decarboxylase, comprising the specific steps as follows:

1) *Agrocybe praecox* (Pers) Fayod is taken as the strain and a seed solution is cultured in a shake flask. The components of seed medium are as follows: yeast extract 3 g/L, soybean peptone 2 g/L, $KH_2PO_4$ 0.5 g/L, $MgSO_4.7H_2O$ 1 g/L, $CaCl_2$ 0.1 g/L, glucose 20 g/L, corn starch 20 g/L, vitamin B 20 mg/L. The pH value is pH 5.0-6.0. The shake flask loading volume is 20-30%. The strain is cultured at 23-28° C., 100-350 rpm for 2-5 days. The mycelium pellets of seed culture are crushed by a mechanical crushing method, and then inoculated with 10-30% of inoculation to next-stage seed culture medium;

2) The seed solution mycelium pellets mechanically crushed are inoculated with 10%-30% inoculation to a 7 L air-lift fermenter for fermentation culture. The liquid fermentation medium consists of the following ingredients: yeast extract 6 g/L, soybean peptone 5 g/L, $KH_2PO_4$ 0.5 g/L, $Na_2HPO_4$ 0.1 g/L, $MgSO_4.7H_2O$ 2 g/L, $CaCl_2$ 1 g/L, glucose 20 g/L, cane sugar 15 g/L, corn starch 20 g/L, vitamin $B_1$ 20 mg/L. The loading volume is 70% and the pH value of the culture medium is adjusted to pH 4.5-6.5. The mycelium pellets are cultured at 23-28° C., 100-350 rpm for 3-5 days after inoculation. The DO is maintained at over 30% by adjusting the airflow speed. This stage is the growth stage of mycelium, and the size of the mycelium pellets is controlled to be less than 0.5 mm.
3) Induced enzyme production stage: when the wet cell mass content of the mycelium reaches 5-30%, the pH value of fermentation broth is adjusted slowly to 3.2-4.0 at the rate of 0.05-1 pH unit per hour. At the same time, $Mn(NO_3)_2$ is added to the final concentration of manganese ions of 0.001 mM of, and the induction production is carried out for 3-15 days. The size of the mycelium pellets are controlled to be not more than 1 mm in the induction process. A feeding medium (soybean peptone: 70-90 g/L, glucose 80-120 g/L, glutathione 10 mM) is added from the 3rd day of induction. After the enzyme production is finished, the fermentation broth and mycelium are collected respectively.
4) The solid-liquid separation is carried out by the method of filtering the fermentation broth and the mycelium through the plate frame filtration, then the supernatant of the fermentation broth is concentrated by ultrafiltration, the small molecule substances in the fermentation broth are removed, and the final concentrated solution is dried by vacuum freeze to obtain enzyme powder, i.e., oxalate decarboxylase powder. *Agrocybe praecox* (Pers.) Fayod mycelium is obtained by frame filtering, and dried by spray drying after homogenization. The protectant is added when spraying, and the edible fungus powder containing oxalate decarboxylase is finally obtained.

Embodiment 14

This embodiment provides a preparation method of enzyme powder and edible fungus powder containing oxalate decarboxylase, comprising the specific steps as follows:
1) *Agrocybe pediades* (Fr.) fayod is taken as the strain and a seed solution is cultured in a shake flask. The components of seed medium are as follows: yeast extract 3 g/L, soybean peptone 3 g/L, $KH_2PO_4$ 1 g/L, $MgSO_4.7H_2O$ 1 g/L, $CaCl_2$ 0.5 g/L, glucose 30 g/L, corn starch 10 g/L, vitamin $B_1$ 8 mg/L. The pH value is pH 5.0-6.0. The shake flask loading volume is 20-30%. The strain is cultured at 23-28° C., 100-350 rpm for 2-5 days. The mycelium pellets of seed culture are crushed by a mechanical crushing method, and then inoculated with 10-30% of inoculation to next-stage seed culture medium.
2) The seed solution mycelium pellets mechanically crushed are inoculated with 10%-30% inoculation to a 7 L mechanical-stirring fermenter for fermentation culture. The liquid fermentation medium consists of the following ingredients: yeast extract 5 g/L, soybean peptone 6 g/L, $KH_2PO_4$ 1 g/L, $Na_2HPO_4$ 0.2 g/L, $MgSO_4.7H_2O$ 2 g/L, $CaCl_2$ 0.1 g/L, glucose 30 g/L, cane sugar 10 g/L, corn starch 15 g/L, vitamin $B_1$ 15 mg/L. The loading volume is 60-70% and the pH value of the culture medium is adjusted to pH 4.5-6.5. The mycelium pellets are cultured at 23-28° C., 100-350 rpm for 3-5 days after inoculation. The DO is maintained at over 30% by adjusting the stirring speed. This stage is the growth stage of mycelium, and the size of the mycelium pellets is controlled to be less than 1 mm.
3) Induced enzyme production stage: when the wet cell mass content of the mycelium reaches 5-30%, the pH value of fermentation broth is adjusted slowly to 2.8-3.2 at the rate of 0.5 pH unit per hour; at the same time, $MnCl_2$ is added to the final concentration of manganese ions of 2 mM, and the induction production is carried out for 3-15 days. The size of the mycelium pellets is controlled to be not more than 0.5 mm in the induction process. A feeding medium (soybean peptone: 70-90 g/L, glucose 80-120 g/L, arginine 20 mM) is added from the 3rd day of induction. After the enzyme production is finished, the fermentation broth and mycelium are collected respectively.
4) The fermentation broth and the mycelia are separated by frame filtration, then the supernatant of the fermentation broth is concentrated by ultra-filtration concentration, small molecules are removed from the fermentation broth, and the final concentrate is dried by vacuum freeze-drying to obtain the enzyme powder, which is oxalate decarboxylase powder. Fermentation mycelium is obtained through frame filtering and dried by vacuum freeze drying. The mycelium obtained after drying is crushed by superfine grinding to obtain the edible fungus powder containing oxalate decarboxylase.

Embodiment 15

This embodiment provides a preparation method of enzyme powder and edible fungus powder containing oxalate decarboxylase, comprising the specific steps as follows:
1) *Agrocybe salicacola* is taken as the strain and cultured by liquid fermentation. The components of seed medium are as follows: yeast extract 3 g/L, soy peptone 2 g/L, $KH_2PO_4$ 2 g/L, $MgSO_4.7H_2O$ 2 g/L, $CaCl_2$ 0.5 g/L, glucose 15 g/L, corn starch 25 g/L and vitamin $B_1$ 15 mg/L. The pH value is pH 5.0-6.0. The flask volume loading volume is 20-30%. The strain is cultured at 23-28° C., 100-350 rpm for 2-5 days. The mycelium pellets of seed culture are crushed by a mechanical crushing method, and then inoculated with 10-30% of inoculation to next-stage culture medium.
2) The seed solution mycelium pellets mechanically crushed are inoculated to a 10 L air-lift fermenter with the inoculation amount of 10-30% for fermentation culture. The liquid fermentation medium consists of the following components: yeast extract 5 g/L, soy peptone 6 g/L, $KH_2PO_4$ 1 g/L, $Na_2HPO_4$ 0.2 g/L, $MgSO_4.7H_2O$ 2 g/L, $CaCl_2$ 0.1 g/L, glucose 30 g/L, corn starch 10 g/L and vitamin $B_1$ 15 mg/L. The loading volume is 60-70% and the pH value of the culture medium is adjusted to pH 4.5-6.5. The mycelium pellets are cultured at 23-28° C., 100-350 rpm for 3-5 days after inoculation. The DO is maintained above 30% by adjusting the stirring speed. This is a mycelium growth stage, and the size of the mycelium pellets is controlled to less than 1 mm;
3) Induced enzyme production stage: when the wet cell mass content of the mycelium reaches 5-30%, the pH value of the fermentation broth is slowly adjusted to pH 3.0-3.6 at the rate of decreasing 1 pH unit per hour, at the same time, induced production is performed 3 to 15 days with $Mn(CH_3COO)_2$ having 50 mM of final concentration of manganese ions, the size of the mycelium pellets is controlled to not more than 0.5 mm in the induction process, a feeding medium (soybean peptone 70-90 g/L, glucose 80-120 g/L, aspartic acid 50 mM) is added from 2nd to 4th day of the induction, and after the enzyme production is finished, the fermentation broth and mycelia are collected respectively;
4) The fermentation broth and the mycelia are separated by plate-frame filtration, then the supernatant of the fermentation broth is concentrated by ultra-filtration concentration, small molecules are removed from the fermentation broth, and the final concentrate is dried by vacuum freeze-drying to obtain enzyme powder, which is oxalate decarboxylase powder. The *Agrocybe salicacola* mycelia obtained by plate-frame filtration are dried by vacuum drying, and the dried mycelia are crushed by ultrafine crushing to obtain the edible fungus powder containing oxalate decarboxylase.

Embodiment 16: Enzymatic Characteristics of *Agrocybe* Oxalate Decarboxylase The activity of oxalate decarboxylase is determined by adopting an HPLC (High Performance Liquid Chromatography) method in the present invention. The specific operation process is as follows: preheating 1.0 mL of 5 mM (millimole concentration) oxalate solution (containing 25 mM citrate buffer, pH3.0) for 10 minutes at 37° C., and then adding 0.01-0.1 ml (the adding volume is determined according to the enzyme concentration) solution or fungus powder suspension containing oxalate decarboxylase to react; adding 50 μL of 2.5M (molar concentration) sulfuric acid to the solution to inactivate the enzyme after reacting 30 minutes; centrifuging the solution immediately and taking supernatant, and determining the concentration of residual oxalate with HPLC. One enzyme activity unit (U) is defined as the enzyme amount required to degrade 1 micromole oxalate per minute on this condition.

The results of activity of oxalate decarboxylase in the enzyme powder and edible fungus powder containing oxalate decarboxylase as prepared in Embodiments 10-15 by adopting HPLC method are shown in table 8 below:

TABLE 8

Determination of activity of different oxalate decarboxylases

| Strain | Activity of enzyme powder (U/mg) | Enzymatic activity of edible fungus powder (U/g) |
| --- | --- | --- |
| Example 10 (*Agrocybe aegerita*) | 50-90 | 600-2354 |
| Example 11 (*Agrocybe aegerita*) | 45-80 | 500-1890 |
| Example 12 (*Agrocybe cylindracea*) | 30-72 | 300-1420 |
| Example 13 (*Agrocybe praecox* (pers.) fayod) | 5-8 | 10-220 |
| Example 14 (*Agrocybe pediades* (Fr.) fayod) | 80-130 | 650-2624 |
| Example 15 (*Agrocybe salicacola*) | 72-127 | 800-3100 |

Taking *Agrocybe aegerita* as an example, *Agrocybe aegerita* mycelia cultured naturally and *Agrocybe aegerita* mycelia (before/after induction) samples cultured by liquid fermentation are respectively weighed with the same weight, then the same volume of pure water is added to them, the solutions are homogenized with a high speed homogenizing machine, the enzyme activities of the homogenates are determined, and the results are shown as table 9. The results show that yield of oxalate decarboxylase is greatly improved after induced fermentation of this patent method, and compared with the natural *Agrocybe aegerita* mycelia or the uninduced liquid fermentation *Agrocybe aegerita*, the activity is improved by a thousand times.

TABLE 9

Comparison of enzyme activities of natural *Agrocybe aegerita* and fermented *Agrocybe aegerita* (induced/uninduced)

| | Enzyme activity (U/g) |
| --- | --- |
| Natural *Agrocybe aegerita* powder | 1-5 |
| Fermented *Agrocybe aegerita* powder (uninduced) | 1-3 |
| Fermented *Agrocybe aegerita* powder (induced) | 600-2354 |

Embodiment 17: Comparison of Oxalate Decarboxylase Yield of Different Edible Fungi The fermentation yields of oxalate decarboxylase of different mycelia are studied by comparing the yield of oxalate decarboxylase of fermentation culture in *Agrocybe aegerita*, *Agrocybe cylindracea*, *Agrocybe praecox* (pers.) fayod, *Agrocybe pediades* (Fr.) Fayod and *Agrocybe salicacola* in embodiments 10-15. The fermentation yields are shown in table 10, the enzyme yields of *Agrocybe aegerita* and *Agrocybe cylindracea* are significantly superior to those of the other three edible fungi. The specific activities of oxalate decarboxylase of *Agrocybe pediades* (Fr) Fayod and *Agrocybe salicacola* are higher than those of *Agrocybe aegerita* and *Agrocybe cylindracea*, but their growth of mycelia is particularly slow and the product amount of mycelia is very small. Considering the economy of fermentation, *Agrocybe aegerita* and *Agrocybe cylindracea* are the most suitable production strains. The inventor would continue to optimize the fermentation conditions to improve the yield of oxalate decarboxylase.

TABLE 10

Comparison of oxalate decarboxylase yield of different strains

| Strain | Enzyme activity (U/L) | Mycelia amount (g/L) |
| --- | --- | --- |
| *Agrocybe aegerita* | 15000-30000 | 12-30 |
| *Agrocybe Cylindracea* | 8000-21000 | 10-22 |
| *Agrocybe praecox* (Pers.) Fayod | 200-1500 | 6-13 |
| *Agrocybe pediades* (Fr.) Fayod | 5500-3200 | 4.6-8.2 |
| *Agrocybe salicacola* | 6100-14500 | 4.4-7.2 |

Embodiment 18: Pilot Scale Enlargement of Fermentation Conditions

The present embodiment provides an enlarged production process of enzyme powder and edible fungus powder containing oxalate decarboxylase, comprising the specific steps as follows:

1) I-stage seed solution preparation stage: *Agrocybe aegerita* is taken as a strain and cultured by shake flask fermentation. The seed medium contains yeast extract 2-4 g/L, soy peptone 1-3 g/L, $KH_2PO_4$ 0.5-3 g/L, $MgSO_4 \cdot 7H_2O$ 0.2-2 g/L, $CaCl_2$ 0.1-1 g/L, glucose 10-30 g/L, corn starch 10-30 g/L and vitamin $B_1$ 5-20 mg/L. The pH value of the culture medium is pH 5.0-6.0. Seeds are cultured in the seed solution at 23-28° C. 100-350 rpm for 2-5 days;
2) II-stage seed solution preparation stage: a 50 L fermenter is adopted for II-stage seed solution culture, and the medium is same as the I-stage seed solution medium. The seed solution is sterilized 30 min with steam of 121° C. and cooled to 23-28° C., the mycelium pellets in the I-stage seed solution of shake flask culture is crushed to less than 1 mm by mechanical crushing, and the crushed mycelium pellets are transferred to the II-stage seed culture medium with the inoculation amount of 10-30% and cultured at 23-28° C., 100-350 rpm for 2-5 days.

2) Fermentation stage: the II-stage seed mycelium pellets crushed mechanically are inoculated to a 500 L mechanical stirring fermenter with the inoculation amount of 10-30% for fermentation culture. The liquid fermentation medium consists of the following components: yeast extract 4-8 g/L, soy peptone 2-6 g/L, $KH_2PO_4$ 0.5-3 g/L, $Na_2HPO_4$ 0.1-1 g/L, $MgSO_4 \cdot 7H_2O$ 0.2-2 g/L, $CaCl_2$ 0.1-1 g/L, glucose 10-30 g/L, cane sugar 10-30 g/L, corn starch 5-20 g/L and vitamin $B_1$ 5-20 mg/L. The loading volume is 60-70% and the pH value of the culture medium is adjusted to pH 4.5-6.5. The mycelium pellets are cultured at 23-28° C., 100-350 rpm for 3-5 days after inoculation. The DO is maintained over 30% by adjusting the stirring speed. This is a mycelium growth stage, and the size of the mycelium pellets is controlled to less than 1 mm;

3) Induced enzyme production stage: when the wet cell mass content of the mycelium reaches 5-30%, the pH value of the fermentation broth is slowly adjusted to pH 3.0-3.6 at the rate of decreasing 0.5-1 pH unit per hour, at the same time, induced production is performed 3-15 days with $MnCl_2$ having 5 mM of final concentration of manganese ions, the size of the mycelium pellets is controlled to not more than 1 mm in the induction process, a feeding medium (soybean peptone 70-90 g/L, glucose 80-120 g/L, arginine 20 mM) is added from 2nd to 4th day of the induction, and after the enzyme production is finished, fermentation broth and mycelia are collected respectively;

4) The fermentation broth and the mycelia are separated by plate-frame filtration, then the supernatant of the fermentation broth is concentrated by ultra-filtration concentration, small molecules are removed from the fermentation broth, and the final concentrate is dried by vacuum freeze-drying to obtain enzyme powder. The *Agrocybe aegerita* mycelia obtained by plate-frame filtration are dried by vacuum drying, and the dried mycelia are crushed by ultrafine crushing to obtain the edible fungus powder containing oxalate decarboxylase.

Embodiment 19: Comparison of Manganese Ion Content of Fermented and Natural Oxalate Decarboxylase Powder Commercial Agrocybe edible fungi (totally 20 kinds of fresh and dried edible fungi such as *Agrocybe aegerita*, *Agrocybe cylindracea*, *Agrocybe praecox* in different areas) are cleaned with clear water, then shredded with scissors and put into a clean ceramic mortar, the edible fungi are ground into powder while liquid nitrogen is added, and then citrate buffer solution (pH 3.0) is added, the edible fungi are continuously ground into paste, the paste is centrifuged at 15000 g for 10 minutes, the supernatant and the sediment are respectively put into new containers, the sediment is freeze-dried into fungus powder containing oxalate decarboxylase, and the supernatant is freeze-dried into enzyme powder containing oxalate decarboxylase. The manganese ion contents of the prepared natural *Agrocybe* edible fungus powder and enzyme powder as well as the enzyme powder and fungus powder containing oxalate decarboxylase prepared by fermentation in embodiments 10-15 are detected. The results are as follows (Table 11):

TABLE 11

| | Manganese ion content | |
|---|---|---|
| | Natural edible fungi | Fermented edible fungi |
| Enzyme powder (mg/g) | Not detected | 1.25-4.65 |
| Edible fungus powder (mg/100 g) | 0.75-1.65 | 4.56-18.59 |
| Enzyme powder (mg/10000 U) | | 0.38-1.72 |
| Edible fungus powder (mg/10000 U) | | 0.73-9.58 |

It can be seen from table 11, the manganese ion content of the oxalate decarboxylase product prepared in the present invention is over 3 times higher than that of the natural Agrocybe oxalate decarboxylase product, but is still in a safety range.

The activities of oxalate decarboxylase prepared in embodiments 10-15 are consistent with the results in embodiments 5-8. It showed that the expression yield of oxalate decarboxylase prepared in embodiments 10-15 are increased, however, the activities of the prepared oxalate decarboxylase are not affected. So, the industrialization of oxalate decarboxylase can be realized.

The invention claimed is:

1. A glycosylated oxalate decarboxylase, wherein: the oxalate decarboxylase is derived from edible fungi of *Agrocybe*, the glycosylated oxalate decarboxylase has an enzyme activity at the pH value of 1.5-7.5; the optimal pH value of the enzyme activity of the oxalate decarboxylase is pH 2.5-3.0; when the oxalate decarboxylase is at the optimal pH value, the optimal activity is 20-200 U/mg;
   the activity at the pH value of 1.5-2.0 is greater than 10% of the optimum activity and the specific activity is more than 2 U/mg;
   the activity at the pH value of 2.0-5.5 is more than 30% of the optimal activity, and the specific activity is more than 6 U/mg; and
   the oxalate decarboxylase is inductively produced by the following liquid fermentation method: after 2-5 days of culture in a fermentation broth of the edible fungi, an acid is added to adjust the pH value to pH 2.0-4.0 under the condition of 0.1-6 mM manganese ions, and then the enzyme is inductively produced; and continuously cultured 7-10 days.

2. The glycosylated oxalate decarboxylase of claim 1, wherein, when the oxalate decarboxylase is at the optimal pH value, the Km value is 0.06 mM.

3. The glycosylated oxalate decarboxylase of claim 1, wherein the oxalate decarboxylase comes from *Agrocybe aegerita*, *Agrocybe cylindracea*, *Agrocybe praecox* (pers.) fayod, *Agrocybe salicacola* or *Agrocybe pediades* (Fr.) Fayod.

4. A method for preparing the oxalate decarboxylase of claim 1, comprising:
   culturing the edible fungi of *Agrocybe* in a fermentation broth after inoculation for 2-5 days;
   adding an acid to adjust the pH value of the fermentation broth to pH 2.0-4.0 and a chemical to adjust manganese ions to 0.1-6 mM, thereby inductively producing the oxalate decarboxylase; and
   culturing continuously for 7-10 days.

5. The method of claim 4, wherein the pH value of the fermentation broth is adjusted to pH 3.2-4.0, pH 3.0-3.6, pH 2.8-3.2, pH 2.6-3.0 or pH 2.0-2.8 during induced enzyme production; and the acid for adjusting the pH value of the fermentation broth is an organic acid or an inorganic acid.

6. The method of claim 4, wherein the added chemical during induced enzyme production include $MnCl_2$, $MnSO_4$, $MnCO_3$, $Mn(NO_3)_2$ and/or $Mn(CH_3COO)_2$; the final concentration of the added manganese ions is 0.1 to 1 mM, 1 to 2 mM, 2 to 4 mM, or 4 to 6 mM.

7. The method of claim 4, wherein a feeding medium is added when the oxalate decarboxylase is being induced, and the feeding medium contains glutamic acid, arginine, aspartic acid or glutathione.

8. The method of claim 4, wherein the culturing of the edible fungi of *Agrocybe* is conducted in a fermenter and the fermenter is a mechanical stirring fermenter or an air-lifting fermenter.

9. The method of claim 4, comprising the following steps: when the edible fungi of *Agrocybe* are cultured to the level that the wet cell mass content reaches 5-20% of the total volume of the fermentation broth, slowly adjusting the pH value of the fermentation broth to pH 2.0-4.0 at the rate of decreasing 0.05-1 pH value unit per hour, at the same time, adding a chemical containing manganese ions, to induce the enzyme for 3-15 days, and after the enzyme production is finished, collecting the fermentation broth and the mycelia respectively.

10. The method of claim 9, further comprising the following steps:
1) culturing *Agrocybe* fungus strains by liquid fermentation, wherein the seed culture medium consists of yeast extract 2-4 g/L, soy peptone 1-3 g/L, $KH_2PO_4$ 0.5-3 g/L, $MgSO_4 \cdot 7H_2O$ 0.2-2 g/L, $CaCl_2$ 0.1-1 g/L, glucose 10-30 g/L, corn starch 10-30 g/L and vitamin $B_1$ 5-20 mg/L; adjusting the pH value of the culture medium to pH 5.0-6.0; subculturing the fungi in the form of mycelium in a seed fermenter at 23 to 28° C., 100-350 rpm for 2-5 days;
2) inoculating the fungi in the form of mycelium to a fermenter for fermentation culture, in a liquid fermentation medium that consists of the following components: yeast extract 4-8 g/L, soy peptone 2-6 g/L, $KH_2PO_4$ 0.5-3 g/L, $Na_2HPO_4$ 0.1-1 g/L, $MgSO_4 \cdot 7H_2O$ 0.2-2 g/L, $CaCl_2$ 0.1-1 g/L, glucose 10-30 g/L, cane sugar 10-30 g/L, corn starch 5-20 g/L and vitamin $B_1$ 5-20 mg/L; adjusting the pH value of the medium to pH 4.5-6.5; culturing the fungi in the form of mycelium at 23 to 28° C. for 3-5 days after inoculation;
3) when the fungi in the form of mycelium are cultured to the level that the wet cell mass content reaches 5-30% of the total volume, slowly adjusting the pH value of the fermentation broth to pH 2.0-4.0 at the rate of decreasing 0.05-1 pH value unit per hour, at the same time, adding a chemical containing manganese ions, to induce the enzyme for 3-15 days, and after the enzyme production is finished, collecting the fermentation broth and the fungi in the form of mycelium mycelia respectively;
4) concentrating the fermentation broth obtained in step 3), purifying the concentrate, removing small molecular substances, and then drying the purified concentrate into powder to obtain an enzyme powder containing oxalate decarboxylase; and filtering, washing, drying and crushing the fungi in the form of mycelium obtained in step 3) into a powder to obtain an edible fungus powder containing oxalate decarboxylase.

11. An enzyme preparation containing the glycosylated oxalate decarboxylase of claim 1.

12. The enzyme preparation of claim 11, wherein the enzyme preparation is an oral preparation.

13. The enzyme preparation of claim 11, wherein the enzyme preparation is edible fungus powder, a feed additive, a feed, a food additive, food, a health-care product, medical food or medicine containing the glycosylated oxalate decarboxylase.

14. A method of treating hyperoxaluria, comprising administering to a subject in need thereof a therapeutically effective amount of a composition, wherein the composition comprises the enzyme preparation of claim 11.

15. A method of treating calcium oxalate urinary calculi, comprising administering to a subject in need thereof a therapeutically effective amount of a composition, wherein the composition comprises the enzyme preparation of claim 11.

* * * * *